United States Patent
de la Torre et al.

(10) Patent No.: US 10,548,580 B2
(45) Date of Patent: Feb. 4, 2020

(54) INSTRUMENT TO CLOSE FASCIA DURING LAPAROSCOPIC SURGERY

(71) Applicants: Roger de la Torre, Columbia, MO (US); Jaya Ghosh, Columbia, MO (US); Ellie Koehly, Columbia, MO (US); Yaw Sarpong, Columbia, MO (US)

(72) Inventors: Roger de la Torre, Columbia, MO (US); Jaya Ghosh, Columbia, MO (US); Ellie Koehly, Columbia, MO (US); Yaw Sarpong, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 140 days.

(21) Appl. No.: 15/736,061

(22) PCT Filed: Jun. 15, 2016

(86) PCT No.: PCT/US2016/037519
§ 371 (c)(1),
(2) Date: Dec. 13, 2017

(87) PCT Pub. No.: WO2016/205292
PCT Pub. Date: Dec. 22, 2016

(65) Prior Publication Data
US 2018/0168561 A1   Jun. 21, 2018

Related U.S. Application Data

(60) Provisional application No. 62/175,532, filed on Jun. 15, 2015.

(51) Int. Cl.
*A61B 17/00* (2006.01)
*A61B 17/04* (2006.01)
*A61B 17/06* (2006.01)

(52) U.S. Cl.
CPC ...... *A61B 17/0057* (2013.01); *A61B 17/0469* (2013.01); *A61B 17/0482* (2013.01); *A61B 17/06004* (2013.01); *A61B 2017/00637* (2013.01); *A61B 2017/00663* (2013.01); *A61B 2017/0472* (2013.01); *A61B 2017/06042* (2013.01)

(58) Field of Classification Search
CPC ............ A61B 17/0057; A61B 17/0469; A61B 17/0482; A61B 17/06004; A61B 2017/00637; A61B 2017/00663; A61B 2017/0472; A61B 2017/06042
See application file for complete search history.

(56) References Cited

U.S. PATENT DOCUMENTS

2012/0053600 A1\* 3/2012 Fortson ............. A61B 17/0057
606/145

\* cited by examiner

*Primary Examiner* — Jocelin C Tanner
(74) *Attorney, Agent, or Firm* — Joseph M. Rolnicki; Evans & Dixon, L.L.C.

(57) ABSTRACT

A surgical instrument can be introduced to the abdominal cavity through a current trocar puncture to place a suture in the deep facia and peritoneum of the anterior abdominal wall. The instrument is lightweight and easy to use, and can be operated quickly and efficiently to close the trocar puncture wound in a simple and economical manner. The instrument is used to suture the deep facia and peritoneum of the anterior abdominal wall on opposite sides of the trocar puncture wound inside the abdomen to close the trocar puncture wound.

15 Claims, 8 Drawing Sheets

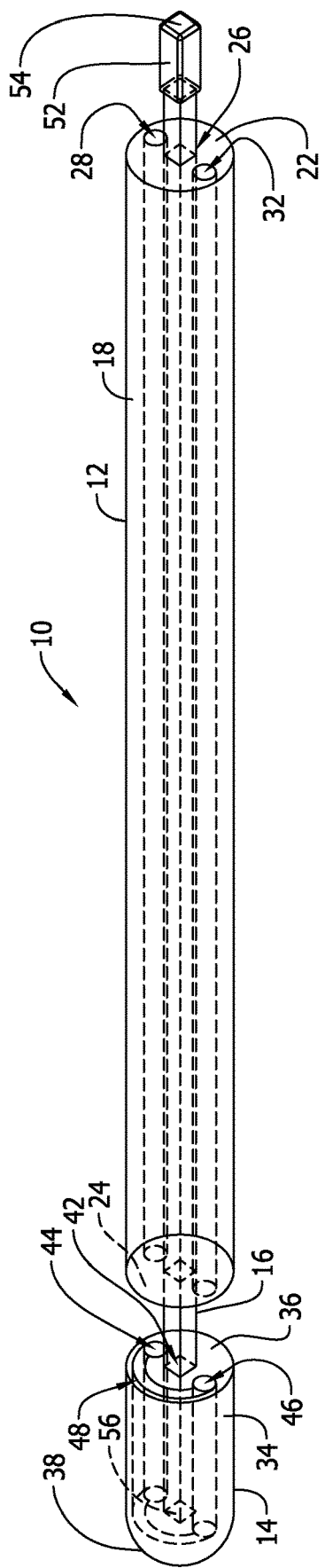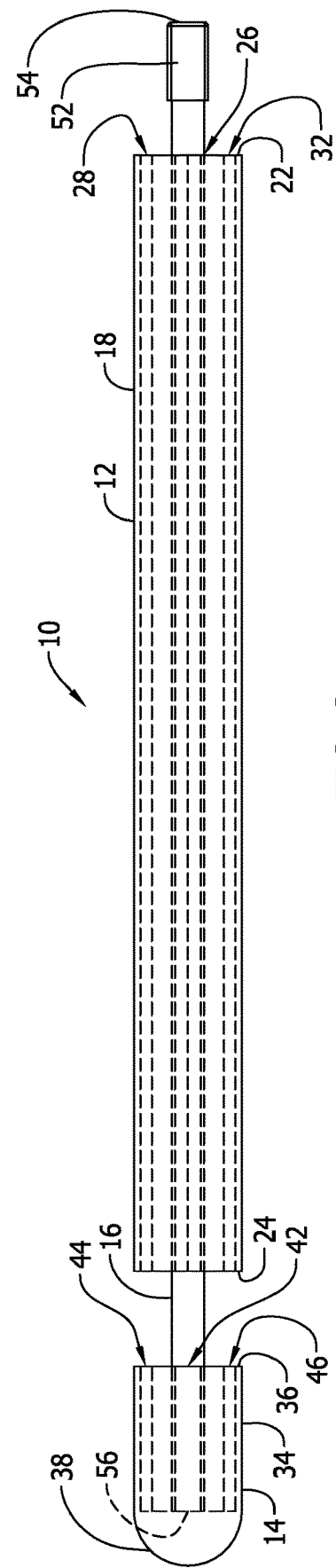

INSTRUMENT TO CLOSE FASCIA DURING LAPAROSCOPIC SURGERY

This application claims the benefit of the Jun. 15, 2015 filing date of provisional patent application Ser. No. 62/175,532.

FIELD

This disclosure pertains to a surgical instrument that is used to suture the deep fascia and peritoneum of the anterior abdominal wall on opposite sides of a trocar port site from inside the abdomen to close the trocar port site.

BACKGROUND

After a laparoscopic surgery procedure a surgeon must often accurately close a trocar port site in the anterior abdominal wall following removal of a large trocar cannula from the port site. Failure to close the site, or an improper closure of the port site can sometimes lead to a herniation of the bowel and subsequent bowel obstruction. Because the standard closure technique for the trocar port site is through a small incision, the present mode for closure of a trocar port site is to reach down to the desired tissue layer with pickups and a loaded needle driver grasp the needle through the abdominal wall and withdraw the needle with the pickups to secure a stitch across the port site. Many times the skin incisions must be extended to accomplish suturing the port site closed.

Current instruments available on the market that are used to close a trocar port site in an anterior abdominal wall are expensive and use complex multi-step processes to close the port site. An instrument that is simple in design and operation is needed.

SUMMARY

The surgical instrument of this disclosure can be introduced to the abdominal cavity through a current trocar puncture to place a suture in the deep fascia and peritoneum of the anterior abdominal wall. The instrument is lightweight and easy to use, and can be operated quickly and efficiently to close the trocar puncture wound in a simple and economical manner.

The instrument includes an elongated housing having a proximal end and a distal end. The housing is divided into three parts, a shorter tubular distal part at the housing distal end, a short adjustable connecting bridge at an intermediate position of the housing, and a longer tubular proximal part that extends from the bridge along the length of the instrument up to the housing proximal end.

The housing distal part functions as a separate housing for at least two catch devices that are received in bores in the distal part and are connected together by a length of suture. The catch devices can be flexible, with or without ridges, and are capable of catching and locking onto a corresponding pitch device housed in the proximal part of the housing.

The pitch devices are constructed as two elongate rigid cylindrical structures with needle point like tips. The tips include features that assist in the pitch devices catching and holding the catch devices. The pitch devices are received in bores through the housing proximal part.

In operation, fascia tissue and the peritoneum to be sutured are caught in a groove surrounding the bridge of the instrument. A first of the pitch devices is then deployed through its bore in the proximal part of the housing. The needle tip of the first pitch device pass through the body tissue surrounding the bridge and enters into a bore in the distal part of the housing holding a first of the catch devices. The needle tip of the first pitch device slides over or into the first catch device. The catch device catches and holds on to the needle tip of the first pitch device. Once the first catch device and first pitch device are joined, they can be moved together by pulling the first pitch device toward the proximal end of the housing. This pulls a first end of the length of suture connected between the catch devices through the tissue. When the first end of the suture has been pulled through the abdominal wall, the instrument can be moved to the opposite side to capture the fascia and peritoneum on the opposite side of the defect that was created by the trocar, and the deployment process of the second pitch device and second catch device can be repeated. The second end of the suture passes through the abdominal wall and both ends of the suture are then available outside the abdominal wall for the physician to complete the process by tying the suture and closing the trocar puncture.

BRIEF DESCRIPTION OF THE DRAWING FIGURES

Further features of the instrument are set forth in the following drawings and detailed description.

FIG. 1 is a perspective view of the elongate housing of the instrument.

FIG. 2 is a side view of the housing of FIG. 1.

DETAILED DESCRIPTION

Figure 3:
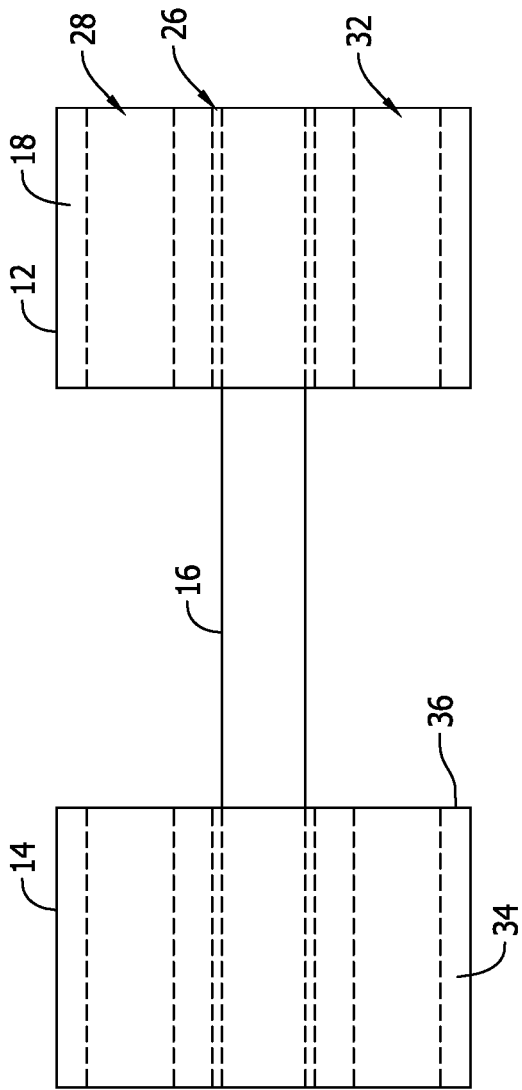
FIG. 3 is an enlarged partial view of the housing.

FIG. 1 is a representation of the surgical instrument housing 10 that is used to close a trocar puncture hole in an abdominal wall following laparoscopic surgery. The instrument housing 10 is basically constructed of three parts that include a proximal part 12, a distal part 14 and a bridge 16.

Each of the housing parts 12, 14, 16 is constructed of biocompatible material typically used in the construction of surgical instruments. The instrument housing 10 has an elongate length that enables the instrument housing to be inserted through a trocar positioned in a puncture hole in an abdominal wall during a laparoscopic surgery procedure to position the instrument distal part 14 in the abdominal cavity with the instrument proximal part 12 projecting out of the trocar.

The housing proximal part 12 has an elongate cylindrical configuration defined by a cylindrical exterior surface 18. The exterior surface 18 has a consistent circumferential dimension that extends along the length of the proximal part 12 between a circular, flat proximal end surface 22 of the proximal part 12 and a circular, flat distal end surface 24 of the proximal part 12. A center bore or bridge bore 26 is formed in the proximal part 12. The center bore 26 extends through the length of the proximal part 12 from the proximal end surface 22 to the distal end surface 24. The center bore 26 has a general rectangular cross-section configuration. A first side bore 28 and a second side bore 32 are also formed in the proximal part 12. The first side bore 28 and second side bore 32 extend through the length of the proximal part 12 from the proximal end surface 22 to the distal end surface 24. The first side bore 28 and the second side bore 32 have general circular cross-section configurations and are positioned on opposite sides of the center bore 26.

The housing distal part 14 has a cylindrical configuration defined by a cylindrical exterior surface 34. The exterior surface 34 of the housing distal part 14 extends between a circular proximal end surface 36 and a semi-spherical distal end surface 38 of the distal part 14. The semi-spherical configuration of the distal end surface 38 of the distal part 14 facilitates the insertion of the instrument 10 through the interior of a trocar, as will be explained. The exterior surface 34 of the distal part 14 and the exterior surface 18 of the proximal part 12 have substantially the same circumferential dimension. The circular proximal end surface 36 of the housing distal part 14 is flat and parallel with the circular distal end surface 24 of the housing proximal part 12. The proximal end surface 36 of the housing distal part 14 and the distal end surface 24 of the housing proximal part 12 can engage flat against each other. The distal part 14 also has a center bore or bridge bore 42 formed in the distal part 14. The center bore 42 extends through the distal part 14 from the proximal end surface 36 of the distal part 14, but the center bore 42 stops short of the distal end surface 38 of the distal part 14. This can best be seen in FIG. 2. The center bore 42 of the distal part 14 has a general rectangular cross-section configuration that is substantially the same as the cross-section configuration of the center bore 26 in the proximal part 12. The distal part 14 also has a first side bore 44 and a second side bore 46 formed in the distal part 14. The first side bore 44 and second side bore 46 extend through the distal part 14 from the proximal end surface 36 of the distal part 14, but stop short of the distal end surface 38 of the distal part 14. This can best be seen in FIG. 2. The first side bore 44 and the second side bore 46 in the distal part 14 have substantially circular cross-section configurations that are substantially the same as the cross-section configurations of the first side bore 28 and the second side bore 30 of the proximal part 12. A general U-shaped slot 48 is also formed in the distal part 14. The slot 48 extends from the proximal end surface 36 of the distal part 14 toward the distal end surface 38 of the distal part 14, but ends short of the distal end surface 38. As can best be seen in FIG. 5, the U-shaped configuration of the slot 48 connects the first side bore 44 and second side bore 46 on opposite sides of the center bore 42 in the distal housing 14 and may be used to house the suture.

The bridge 16 has an elongate length that is greater than the combined lengths of the proximal part 12 and the distal part 14. The length of the bridge 16 extends from an enlarged handle 52 formed on the bridge 16 at a proximal end surface 54 of the bridge to a distal end surface 56 of the bridge 16. The length of the bridge 16 between the handle 52 and the bridge distal end surface 56 has a general rectangular cross-section configuration that is dimensioned to be received in and slide through the center bore 26 of the proximal part 12 and be received in the center bore 42 of the distal part 14. A distal end portion of the bridge 16 that is received in the center bore 42 of the distal part 14 is secured to the distal part 14, thereby securing the distal part 14 to the bridge 16. The rectangular cross-section configuration of the bridge 16 in the center bore 26 of the proximal part 12 prevents the bridge 16 from rotating in the center bores 26 and 42. This also keeps the first side bore 28 and second side bore 32 of the proximal part aligned with the first side bore 44 and the second side bore 46 of the distal part 14. By manually gripping the bridge handle 52 and moving the handle 52 toward the proximal end surface 22 of the proximal part 12, the distal part 14 is moved away from the distal end surface 24 of the proximal part 12. Manually gripping the bridge handle 52 and moving the bridge handle 52 away from the proximal end surface 22 of the proximal part 12 causes the distal part 14 to move toward the distal end surface 24 of the proximal part 12.

FIG. 3 is an enlarged partial view of a portion of the proximal part 12 adjacent the proximal part distal end surface 24, a portion of the distal part 14 adjacent the distal part proximal end surface 36, and a portion of the bridge 16.

Figure 4:
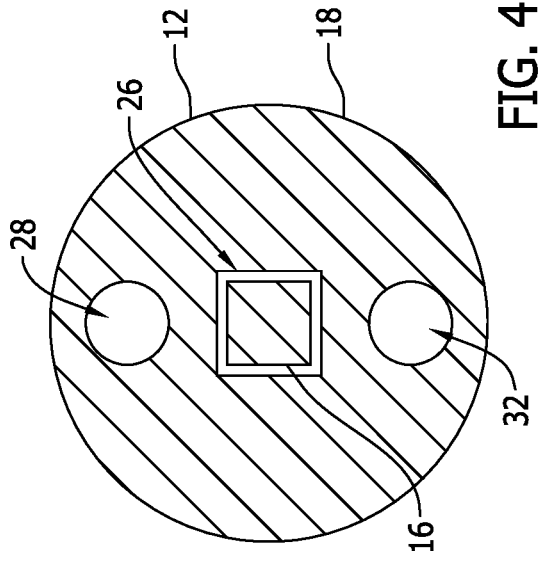
FIG. 4 is a cross-section view of the housing in the plane A-A of FIG. 3.

FIG. 4 is a cross-section view in the plane of the line A-A in FIG. 3 showing the relative positions of the center bore 26, first side bore 28, second side bore 32 and the bridge 16 in the portion of the proximal part 12 shown in FIG. 3.

Figure 5:
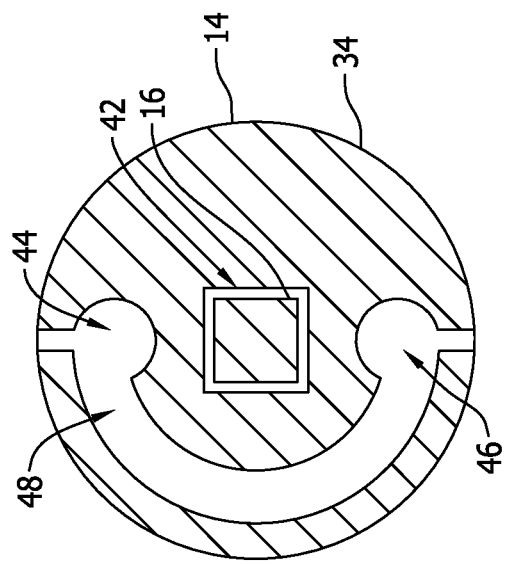
FIG. 5 is a cross-section view of the housing in the plane B-B of FIG. 3.

FIG. 5 is a cross-section view in the plane of the line B-B in FIG. 3 showing the relative positions of the center bore 42, the first side bore 44, the second side bore 46, the bridge 16 and the slot 48 in the portion of the distal part 14 shown in FIG. 3.

Figure 6:
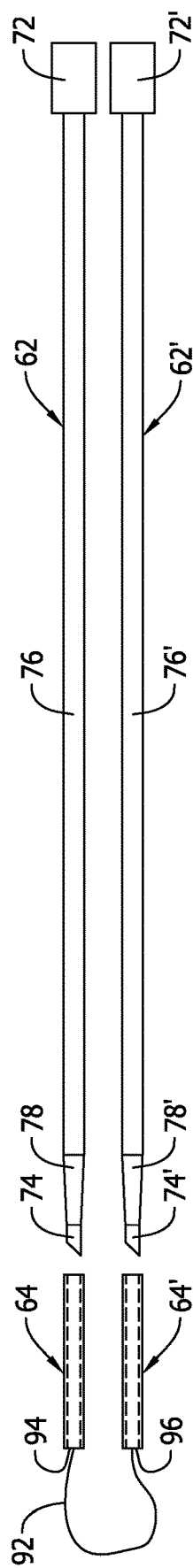
FIG. 6 is a side view of the pitch devices and catch devices of the instrument.

FIG. 6 is a side view of a first pitch device 62, a second pitch device 62', a first catch device 64, a second catch device 64' and a length of suture that is secured to the first catch device 64 and the second catch device 64'. Because the first pitch device 62 and the second pitch device 62' have substantially the same constructions, only the first pitch device 62 is described in detail herein. Corresponding portions of the second pitch device 62' are labeled with the same reference numbers used in the description of the first pitch device 62, with the reference numbers being followed by a prime ('). Additionally, because the constructions of the first catch device 64 and the second catch device 64' are substantially the same, only the first catch device 64 is described in detail herein. Corresponding portions of the second catch device 64' are labeled with the same reference numbers used in the description of the first catch device 64, with the reference numbers being following by a prime (').

The first pitch device 62 has a slender, elongate construction that extends from a manual handle 72 at a proximal end of the first pitch device 62 to a needle tip 74 at a distal end of the first pitch device 62. A majority of the length of the first pitch device 62 is comprised of a cylindrical rod 76. The rod 76 has a cylindrical circumference dimensioned to be received in and slide through the first side bore 28 of the housing proximal part 12 and the first side bore 44 of the housing distal part 14. The length of the rod 76 extends from the handle 72 to a tapered portion 78 that connects the rod 76 to the needle tip 74.

The first catch device 64 has a tubular length with a cylindrical exterior surface 82. The length of the first catch device 64 extends from a circular proximal end surface 84 to a circular distal end surface 86. The first catch device 64 has a circumferential dimension and a length dimension that enables the first catch device 64 to be received in the first side bore 44 of the housing distal part 14. The first catch device 64 has a cylindrical interior bore surface 88. The interior bore surface 88 has a circumferential dimension that is larger than a circumferential dimension of the needle tip 74 of the first pitch device 62, but is smaller than the circumferential dimension of the rod 76 of the first pitch device 62. The first catch device 64 is constructed of a resilient material that allows the cylindrical interior bore surface 88 of the first catch to expand slightly.

A length of suture 92 extends between the first catch device 64 and the second catch device 64'. The length of suture 92 is actually much longer than represented in FIG. 6. A first end 94 of the suture 92 is secured to the first catch device 64 and a second end 96 of the suture 92 is secured to the second catch device 64'. The length of the suture 92 between the first end 94 and the second end 96 is sufficient to enable the suture 92 to extend across a trocar puncture wound in an abdominal wall with the suture first end 94 and the suture second end 96 extending through the abdominal wall on opposite sides of the puncture wound to the exterior of the abdomen. The suture 92 is stored in the slot 48 of the housing distal part 14 with the first catch device 64 stored in the first side bore 44 of the distal part 14 and the second catch device 64' stored in the second side bore 46 of the distal part 14.

Figure 7:
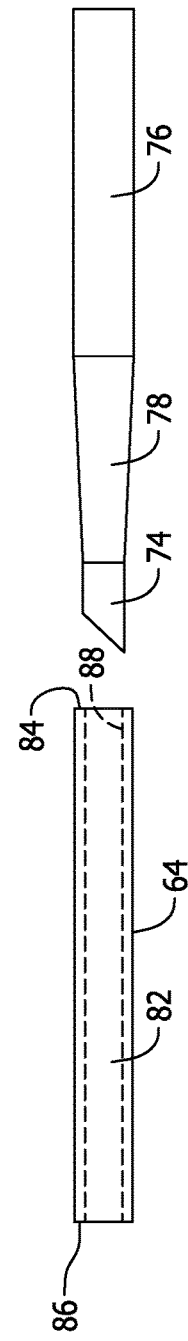
FIG. 7 is an enlarged partial view of a needle tip of one of the pitch devices and a catch device.
Figure 8:
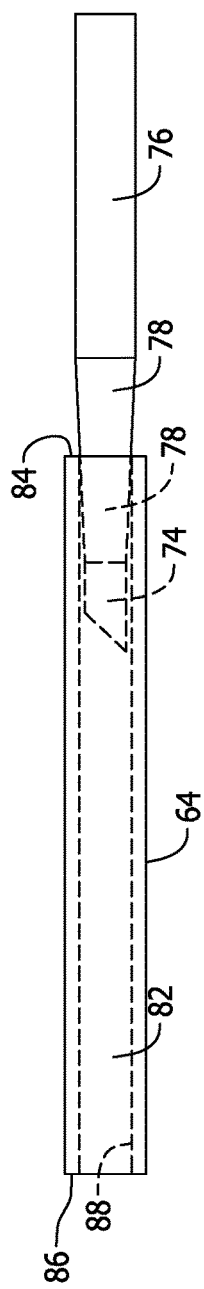
FIG. 8 is an enlarged partial view of a needle tip of one of the pitch devices caught by one of the catch devices.

Referring to FIGS. 7 and 8, the relative dimensions of the first pitch device 62 and the first catch device 64 enable the needle tip 74 of the first pitch device 62 to be inserted into the bore defined by the cylindrical interior surface 88 of the first catch device 64. As represented in FIG. 8, as the needle tip 74 of the first pitch device 62 is moved further into the interior bore of the first catch device 64, the tapered portion 78 of the first pitch device 62 engages with the cylindrical interior surface 88 of the first catch device 64. Further movement of the needle tip 74 into the cylindrical interior surface 88 of the first catch device 64 causes the interior surface 88 to resiliently stretch outwardly over the tapered portion 78 of the first pitch device 62. The resilient stretching of the cylindrical interior surface 88 of the first catch device 64 over the tapered portion 78 of the first pitch device 62 causes the first catch device 64 to catch and hold to the first pitch device 62.

In use of the instrument, the bridge handle 52 is grasped and manually moved away from the proximal end surface 22 of the housing proximal part 12 until the proximal end surface 36 of the distal part 14 engages with the distal end surface 24 of the proximal part 12. The instrument housing 10 is then ready to be inserted through a trocar that has been previously positioned through an abdominal wall. The instrument housing 10 slides through the interior of the trocar guided by the semi-spherical distal end surface 38 of the distal part 14. The instrument housing 10 is continued to be moved through the trocar until the distal part 14 and a portion of the proximal part 12 extends from the trocar and into the abdominal cavity.

With the distal part 14 and a portion of the proximal part 12 positioned in the abdominal cavity, the trocar can then be removed from the puncture wound in the abdominal wall. This causes the puncture wound in the abdominal wall to contract and engage around the portion of the proximal part 12 positioned inside the abdominal cavity.

The handle 52 of the bridge 16 is then moved toward the proximal end surface 22 of the proximal part 12. This causes the bridge 16 to move through the center bore 26 of the proximal part 12 and push the distal part 14 away from the proximal part 12 in the abdominal cavity. The movement of the distal part 14 away from the proximal part 12 exposes a portion of the bridge 16 that extends between the distal end surface 24 of the proximal part 12 and the proximal end surface 36 of the distal part 14.

The proximal part 12 is then pulled away from the puncture wound in the abdominal wall until the portion of the bridge 16 extending between the distal end surface 24 of the proximal part 12 and the proximal end surface 36 of the distal part 14 is moved into the puncture wound. This causes the puncture wound to contract around the portion of the bridge 16 extending between the distal end surface 24 of the proximal part 12 and the proximal end surface 36 of the distal part 14.

The bridge handle 52 is then moved away from the proximal end surface 22 of the proximal part 12 causing the proximal end surface 36 of the distal part 14 to move toward the distal end surface 24 of the proximal part 12. The movement of the bridge handle 52 is continued until the portion of the abdominal wall surrounding the trocar puncture wound and surrounding the bridge 16 is engaged and secured between the distal end surface 24 of the proximal part 12 outside the abdomen and the proximal end surface 36 of the distal part 14 inside the abdomen.

With the portion of the abdominal wall surrounding the trocar puncture wound secured between the distal end surface 24 of the proximal part 12 and the proximal end surface 36 of the distal part 14, the first pitch device 62 and the second pitch device 62' are then deployed. The handle 72 of the first pitch device 62 is moved toward the proximal end surface 22 of the proximal part 12. This causes the needle tip 74 of the first pitch device 62 to penetrate through the portion of the abdominal wall secured between the distal end surface 24 of the proximal part 12 and the proximal end surface 36 of the distal part 14. The needle tip 74 then moves into the first side bore 44 of the distal housing and into the first catch device 64. The movement of the needle tip 74 of the first pitch device 62 into the first catch device 64 is continued until the tapered portion 78 of the first pitch device 62 is pushed into and engaged by the cylindrical interior surface 88 of the first catch device 64, whereby the first catch device 64 catches the first pitch device 62.

The instrument is physically moved to similarly engage the deep fascia and peritoneum of the abdominal wall on the opposite side of the trocar puncture wound. The second pitch device 62' is then deployed in the same manner as the first pitch device 62 until the needle tip 74' of the second pitch device 62' moves into the interior bore of the second catch device 64' and the interior surface 88' of the second catch device 64' engages against the tapered portion 78' of the second pitch device 62' and thereby catches the second pitch device 62'.

The first pitch device 62 and the second pitch device 62' can then be withdrawn through the proximal part 12 by moving the handles 72, 72' of the respective first pitch device 62 and second pitch device 62' away from the proximal end surface 22 of the proximal part 12. This causes the first pitch device 62 and the second pitch device 62' to pull the respective first catch device 64 and second catch device 64' from the respective first side bore 44 and second side bore 46 of the distal part 12 and through the portion of the abdominal wall grasped between the distal end surface 24 of the proximal part 12 and the proximal end surface 36 of the distal part 14. This in turn pulls the suture 92 from the slot 48 in the distal part 14 and pulls the suture first end 94 and the suture second end 96 through the abdominal wall to the exterior of the abdomen.

With the suture first end 94 and suture second end 96 now outside the abdominal wall and the suture 92 extending across the trocar puncture wound in the abdominal cavity, the suture first end 94 and the suture second end 96 can be tied off, thereby completing the stitch of the trocar puncture wound.

Figure 9:
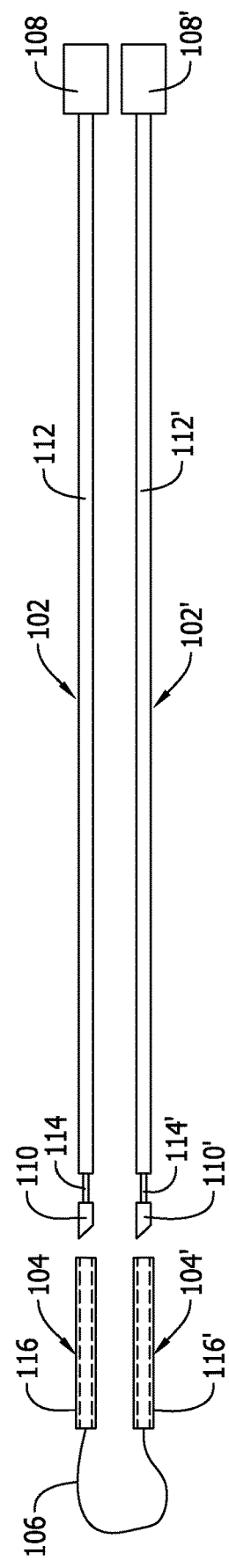
FIG. 9 is a side view of further embodiments of pitch devices and catch devices of the instrument.
Figure 10:
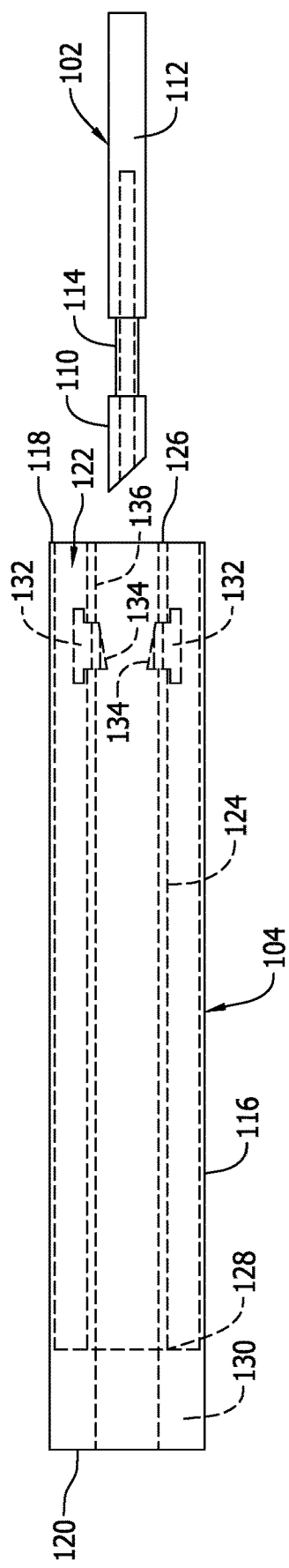
FIG. 10 is an enlarged partial view of a needle tip of one of the pitch devices represented in FIG. 9 and one of the catch devices represented in FIG. 9.
Figure 11:
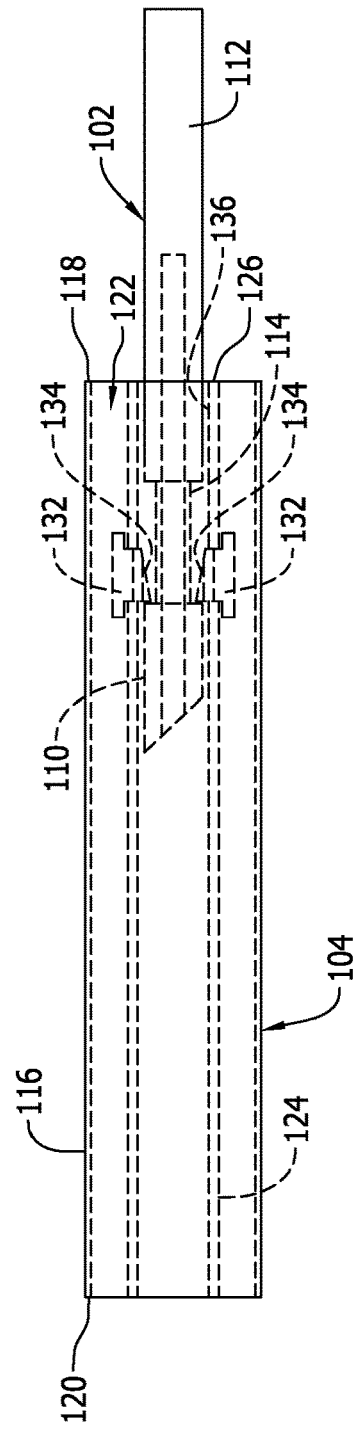
FIG. 11 is an enlarged partial view of a needle tip of one of the pitch devices represented in FIG. 9 caught by one of the catch devices represented in FIG. 9.

Further embodiments of pitch devices and catch devices that can be used in the instrument housing 10 are represented in FIGS. 9-11.

FIG. 9 is a side view of a first pitch device 102, a second pitch device 102', a first catch device 104, a second catch device 104' and a length of suture 106 that is secured to the first catch device 104 and the second catch device 104'. Because the first pitch device 102 and the second pitch device 102' have substantially the same constructions, only the first pitch device 102 is described in detail herein. Corresponding portions of the second pitch device 102' are labeled with the same reference numbers used in the description of the first pitch device 102, with the reference numbers being following by a prime ('). Additionally, because the constructions of the first catch device 104 and the second catch device 104' are substantially the same, only the first catch device 104 is described in detail herein. Corresponding portions of the second catch device 104' are labeled with the same reference numbers used in the description of the first catch device 104, with the reference numbers being followed by a prime (').

As with the construction of the first described version of the first pitch device 62, the first pitch device 102 represented in FIG. 9 has a slender, elongate construction that extends from a manual handle 108 at a proximal end of the first pitch device 102 to a needle tip 110 at a distal end of the first pitch device 102. A majority of the length of the first pitch device 102 is comprised of a cylindrical rod 112. The length of the rod 112 extends from the handle 108 to the needle tip 110. The rod 112 has a cylindrical circumference dimensioned to be received in and slide through the first side bore 28 of the housing proximal part 12 and the first side bore 44 of the housing distal part 14. The rod 112 differs from the rod 76 of the first described first pitch device 62 by a circumferential notch 114 formed in the rod 112 adjacent the needle tip 110. The notch 114 extends completely around the circumference of the rod 112.

The first catch device 104 represented in FIG. 9 is similar in construction to the first described first catch device 64 in that it has a tubular length with a cylindrical exterior surface 116. Referring to FIG. 10, the length of the first catch device 104 extends from a circular proximal end surface 118 to a circular distal end surface 120. The first catch device 104 has a circumferential dimension and a length dimension that enables the first catch device 104 to be received in the first side bore 44 of the housing distal part 14. The first catch device 104 has a cylindrical interior bore 122 that contains a resilient tube 124. The tube 124 has a length that extends from a circular proximal end surface 126 of the tube to a circular, distal end 128 of the tube. The tube distal end 128 is integral with a cylindrical distal end wall 130 of the first catch device 104. The wall 130 connects the tube 124 to the distal end surface of the first catch device 104. The tube 124 has a pair of diametrically opposed tabs 132 formed on the tube 124 adjacent the tube proximal end surface 126. The tabs 132 have inclined surfaces 134 that oppose each other. The inclined surfaces 134 extend radially inwardly from an interior surface 136 of the tube 124 as the inclined surfaces 134 extend toward the tube distal end 128. The interior surface 136 of the tube 124 has an interior diameter dimension that is larger than an exterior diameter dimension of the needle tip 110 of the first pitch device 102. The opposed inclined surfaces 134 of the tabs 132 have a radial distance dimension between the surfaces that is smaller than the exterior diameter dimension of the needle tip 110.

The length of suture 106 extending between the first catch device 104 and the second catch device 104' is substantially the same as the suture 92 described earlier and is stored in the housing distal part 14 in the same manner as the previously described suture 92.

Referring to FIG. 11, the relative dimensions of the first pitch device 102 and the first catch device 104 enable the needle tip 110 of the first pitch device 102 to be inserted into the tube 124 of the first catch device 104. As represented in FIG. 11, as the needle tip 110 of the first pitch device 102 is moved further into the interior bore of the tube 124, the needle tip 110 engages between the opposed inclined surfaces 134 of the tabs 132. As the needle tip 110 is inserted further into the tube 124 the needle tip 110 slides across the opposed inclined surfaces 134 and pushes the inclined surfaces 134 away from each other against the resilience of the tube 124. The movement of the needle tip 110 into the tube 124 is continued until the inclined surfaces 134 are moved into the circumferential notch 114 of the rod 112. The resilience of the tube 124 then causes the tabs 132 to move toward each other into the circumferential notch 114 of the rod 112. This causes the first catch device 104 to catch and hold to the first pitch device 102.

The first pitch device 102, the second pitch device 102', the first catch device 104, the second catch device 104' and the suture 106 represented in FIG. 9 are employed with the instrument housing 10 to close a trocar puncture in the same manner as the pitch devices and catch devices represented in FIG. 6 and described earlier.

Figure 12:
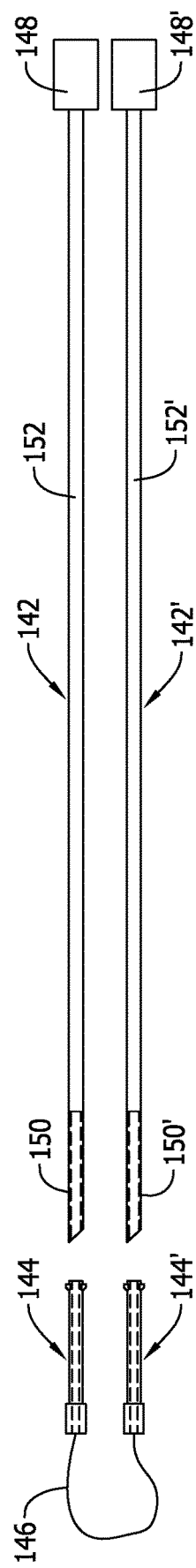
FIG. 12 is a side view of further embodiments of pitch devices and catch devices of the instrument.

Still further embodiments of pitch devices and catch devices that can be used in the instrument housing 10 are represented in FIGS. 12-16. FIG. 12 is a side view of a first pitch device 142, a second pitch device 142', a first catch device 144, a second catch device 144' and a length of suture 146 that is secured to the first catch device 144 and the second catch device 144'. Because the first pitch device 142 and the second pitch device 142' have substantially the same constructions, only the first pitch device 142 is described in detail herein. Corresponding portions of the second pitch device 142' are labeled with the same reference numbers used in the description of the first pitch device 142, with the reference numbers being followed by a prime ('). Additionally, because the constructions of the first catch device 144 and the second catch device 144' are substantially the same, only the first catch device 144 is described in detail herein. Corresponding portions of the second catch device 144' are labeled with the same reference numbers used in the description of the first catch device 144, with the reference numbers being followed by a prime (').

Figure 13:
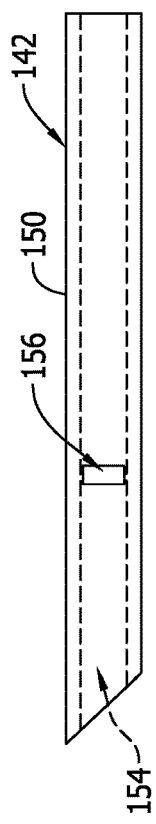
FIG. 13 is an enlarged partial view of a needle tip of one of the pitch devices represented in FIG. 12.

As with the construction of the first described version of the first pitch device 62, the first pitch device 142 represented in FIG. 12 has a slender, elongate construction that extends from a manual handle 148 at a proximal end of the first pitch device 142 to a needle tip 150 at a distal end of the first pitch device 142. A majority of the length of the first pitch device 142 is comprised of a cylindrical rod 152. The length of the rod 152 extends from the handle 148 to the needle tip 150. The rod 152 has a cylindrical circumference dimensioned to be received in and slide through the first side bore 28 of the housing proximal part 12 and the first side bore 44 of the housing distal part 14. The rod 152 differs from the rod 76 of the first described first pitch device 62 by an interior bore 154 formed into the needle tip 150 of the rod as represented in FIG. 13. The interior bore 154 extends only a short distance into the interior of the rod 152 from the needle tip 150. Additionally, a pair of openings 156 are formed into diametrically opposite sides of the rod 152 adjacent the needle tip 150. The pair of openings 156 extend into the rod 152 and intersect with the interior bore 154.

Figure 14:
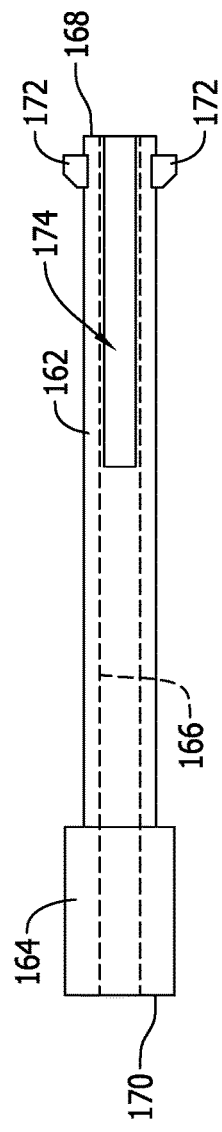
FIG. 14 is an enlarged view of one of the catch devices represented in FIG. 12.

The first catch device 144 is represented in FIG. 14. The first catch device 144 has a tubular length with a proximal cylindrical exterior surface portion 162 and a distal cylindrical exterior surface portion 164. The length of the first catch device 144 extends from a generally circular proximal end surface 168 to a circular distal end surface 170. The first catch device proximal exterior surface portion 162 has a circumferential dimension and a length dimension that enables the proximal exterior surface portion 162 to be inserted into and received in the interior bore 154 of the needle tip 150. The distal exterior surface portion 164 of the first catch device 144 has a circumferential dimension and a length dimension that enables the distal end surface portion 164 to be received in the first side bore 44 of the housing distal part 14. A cylindrical interior bore surface 166 extends through the length of the first catch device 144. A pair of tabs 172 project outwardly from diametrically opposite sides of the first catch device proximal exterior surface portion 162 adjacent the proximal end surface 168 of the first catch device 144. The tabs 172 are shaped and dimensioned to fit into the openings 156 in the opposite sides of the needle tip 150 of the first pitch device 142. A pair of slots 174 are formed through opposite sides of the first catch device proximal exterior surface portion 162. The slots 174 are positioned between the pair of tabs 72 and extend through the interior bore surface 166 of the first catch device 144. The slots 174 enable the tabs 172 to resiliently flex toward each other.

The length of suture 146 extending between the first catch device 144 and the second catch device 144' is substantially the same as the suture 92 described earlier and is stored in the housing distal part 14 in the same manner as the previously described suture 92.

Figure 15:
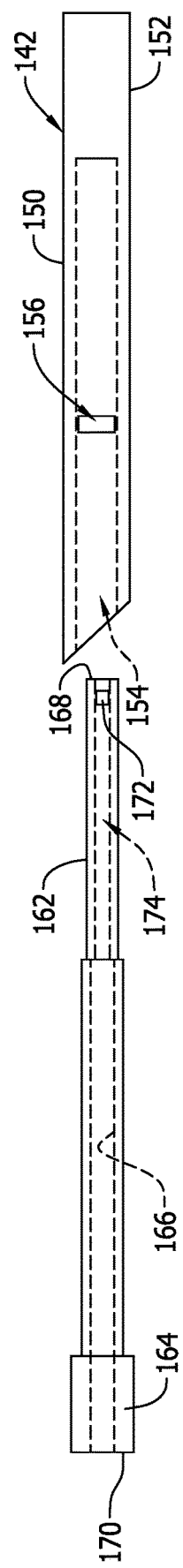
FIG. 15 is an enlarged partial view of a needle tip of one of the pitch devices represented in FIG. 12 and an associated catch device.
Figure 16:
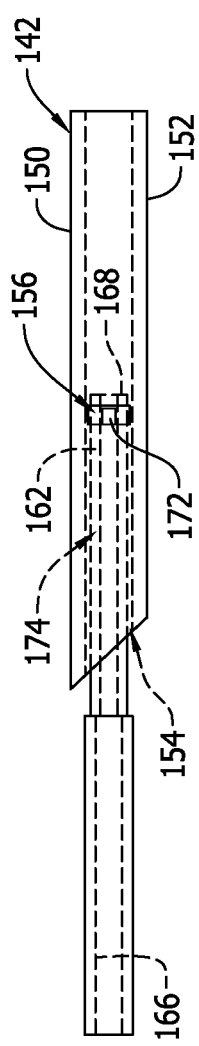
FIG. 16 is an enlarged partial view of the needle tip of FIG. 15 caught by the catch device of FIG. 15.

Referring to FIGS. 15 and 16, the relative dimensions of the interior bore 154 of the needle tip 150 of the first pitch device 142 and the proximal exterior surface portion 162 of the first catch device 144 enable the proximal exterior surface portion 162 of the first catch device 144 to be inserted into the interior bore 154 of the first pitch device 142. Prior to insertion of the proximal exterior surface portion 162 of the first catch device 144 into the interior bore 154 of the first pitch device 142, the first catch device 144 and the first pitch device 142 are positioned relative to each other as represented in FIG. 15. This aligns the tabs 172 of the first catch device 144 with the openings 156 of the first pitch device 142. As the first pitch device 142 is moved toward the first catch device 144, the first catch device proximal exterior surface portion 162 enters into the interior bore 154 of the first pitch device 142. As the tabs 172 enter the interior bore 154, they are pushed resiliently toward each other by the interior surface of the first pitch device interior bore 154. The first pitch device 142 is continued to be moved toward the first catch device 144 until the tabs 172 slide into the openings 156 of the first pitch device 142. The resilience of the tabs 172 provided by the slots 174 through the first catch device proximal exterior surface portion 162 enables the tabs 172 to move outwardly and engage in the opening 156 of the first pitch device 142. This causes the first catch device 144 to catch and hold to the first pitch device 142.

The first pitch device 142, the second pitch device 142', the first catch device 144', the second catch device 144' and the suture 146 represented in FIG. 12 are employed with the instrument housing 10 to close a trocar puncture in the same manner as the pitch devices and catch devices represented in FIG. 6 and described earlier.

As seen from the above description, there are different embodiments of the pitch devices and their associated catch devices. From a design perspective, the inner diameter of the pitch device could either be larger than the outer diameter of the catch device, or the inner diameter of the catch device could be larger than the outer diameter of the pitch device.

Although the surgical instrument has been described herein as being used to stitch closed a trocar puncture wound in an abdominal wall, there are many other equivalent uses for the surgical instrument.

For example, it is possible to use the surgical instrument to close primary ventral hernias such as umbilical hernias. Often an umbilical hernia is no bigger than the size of a quarter. The surgical instrument could be used by making a small skin incision over the hernia and then inserting the instrument through the skin incision and inserting the distal part 14 of the instrument housing 10 and a portion of the proximal part 12 of the instrument housing through the hernia. The surgical instrument is then used as discussed earlier to place a suture on opposite sides of the hernia defect and then tying off the suture as described above, allowing the edges of the hernia defect to be approximated.

As various modifications could be made in the construction of the apparatus and its method of operation herein described and illustrated without departing from the scope of the invention, it is intended that all matter contained in the foregoing description or shown in the accompanying drawings shall be interpreted as illustrative rather than limiting. Thus, the breadth and scope of the present disclosure should not be limited by any of the above described exemplary embodiments, but should be defined only in accordance with the following claims appended hereto and their equivalents.

The invention claimed is:
1. A surgical instrument comprising:
an instrument housing comprising a proximal part and a distal part;
the proximal part having a length between a proximal end surface of the proximal part and a distal end surface of the proximal part, the proximal part having a bridge bore extending through the length of the proximal part from the proximal end surface of the proximal part to the distal end surface of the proximal part, the proximal part having a side bore extending through the length of the proximal part from the proximal end surface of the proximal part to the distal end surface of the proximal part;
the distal part having a length between a proximal end surface of the distal part and a distal end surface of the distal part, the distal part having a side bore extending into the distal part from the proximal end surface of the distal part, the distal part having a slot extending into the distal part from the proximal end surface of the distal part, the slot being positioned adjacent the side bore and connecting to the side bore of the distal part;

a bridge adjustably connecting the proximal part and the distal part, the bridge having a length that extends from a proximal end surface of the bridge, through the bridge bore of the proximal part and to a distal end of the bridge that is secured to the distal part, the bridge adjustably connecting the proximal part and the distal part with the side bore of the proximal part aligned with the side bore of the distal part, the bridge being adjustable to selectively move the proximal part and the distal part away from each other and the bridge being adjustable to selectively move the proximal part and the distal part toward each other;

a pitch device in the side bore of the proximal part, the pitch device having a length that extends from a handle of the pitch device, through the side bore of the proximal part to a tip of the pitch device positioned inside the side bore of the proximal part;

a catch device in the side bore of the distal part;

a suture in the slot of the distal part, the suture being connected to the catch device;

the catch device being operable to catch and hold to the tip of the pitch device in response to the handle of the pitch device being moved toward the proximal end surface of the proximal part and the tip of the pitch device being moved out of the side bore of the proximal part and into the side bore of the distal part and engaging with the catch device;

the catch device having a resilient tube with a interior surface that surrounds an interior bore of the catch device and a pair of tabs that project inwardly toward each other from the interior surface and into the interior bore; and, the pitch device having a circumferential notch adjacent the tip of the pitch device, the circumferential notch being dimensioned to receive the tabs of the catch device in the circumferential notch when the tip of the pitch device is inserted into the tube of the catch device whereby the catch device catches and holds to the pitch device.

2. The surgical instrument of claim 1, further comprising:
the side bore extending through the length of the proximal part being a first side bore extending through the length of the proximal part, the proximal part having a second side bore extending through the length of the proximal part from the proximal end surface of the proximal part to the distal end surface of the proximal part;
the side bore extending into the distal part being a first side bore extending into the distal part from the proximal end surface of the distal part, the distal part having a second side bore extending into the distal part from the proximal end surface of the distal part;
the pitch device in the side bore of the proximal part being a first pitch device in the first side bore of the proximal part;
a second pitch device in the second side bore of the proximal part, the second pitch device having a length that extends from a handle of the second pitch device, through the second side bore of the proximal part to a tip of the second pitch device positioned inside the second side bore of the proximal part;
the catch device in the side bore of the distal part being a first catch device in the first side bore of the distal part;
a second catch device in the second side bore of the distal part;
the suture in the slot of the distal part being connected to the first catch device and the second catch device; and,
the second catch device being operable to catch and hold to the tip of the second pitch device in response to the handle of the second pitch device being moved toward the proximal end surface of the proximal part and the tip of the second pitch device being moved out of the second side bore of the proximal part and into the second side bore of the distal part and engaging with the second catch device.

3. The surgical instrument of claim 2, further comprising:
the bridge bore extending through the length of the proximal part extending through a center of the proximal part and the first side bore of the proximal part and the second side bore of the proximal part being on opposite sides of the bridge bore of the proximal part.

4. The surgical instrument of claim 2, further comprising:
the slot extending into the distal part from the proximal end surface of the distal part connecting the first side bore of the distal part and the second side bore of the distal part.

5. The surgical instrument of claim 2, further comprising:
the bridge adjustably connecting the proximal part and the distal part with the first side bore of the proximal part aligned with the first side bore of the distal part and with the second side bore of the proximal part aligned with the second side bore of the distal part.

6. The surgical instrument of claim 2, further comprising:
the bridge being adjustable to selectively move the proximal part and the distal part away from each other in response to the proximal end surface of the bridge being moved toward the proximal end surface of the proximal part and the bridge being adjustable to selectively move the proximal part and the distal part toward each other in response to the proximal end surface of the bridge being moved away from the proximal end surface of the proximal part.

7. The surgical instrument of claim 2, further comprising:
the first pitch device length extends from the handle of the first pitch device positioned outside the proximal part; and,
the second pitch device length extends from the handle of the second pitch device positioned outside the proximal part.

8. A surgical instrument comprising:
an instrument housing comprising a proximal part and a distal part;
the proximal part having a length between a proximal end surface of the proximal part and a distal end surface of the proximal part, the proximal part having a bridge bore extending through the length of the proximal part from the proximal end surface of the proximal part to the distal end surface of the proximal part, the proximal part having a side bore extending through the length of the proximal part from the proximal end surface of the proximal part to the distal end surface of the proximal part;
the distal part having a length between a proximal end surface of the distal part and a distal end surface of the distal part, the distal part having a side bore extending into the distal part from the proximal end surface of the distal part, the distal part having a slot extending into the distal part from the proximal end surface of the distal part, the slot being positioned adjacent the side bore and connecting to the side bore of the distal part;
a bridge adjustably connecting the proximal part and the distal part, the bridge having a length that extends from a proximal end surface of the bridge, through the bridge bore of the proximal part and to a distal end of the bridge that is secured to the distal part, the bridge adjustably connecting the proximal part and the distal part with the side bore of the proximal part aligned with the side bore of the distal part, the bridge being adjustable to selectively move the proximal part and the distal part away from each other and the bridge being adjustable to selectively move the proximal part and the distal part toward each other;

a pitch device in the side bore of the proximal part, the pitch device having a length that extends from a handle of the pitch device, through the side bore of the proximal part to a tip of the pitch device positioned inside the side bore of the proximal part;

a catch device in the side bore of the distal part;

a suture in the slot of the distal part, the suture being connected to the catch device;

the catch device being operable to catch and hold to the tip of the pitch device in response to the handle of the pitch device being moved toward the proximal end surface of the proximal part and the tip of the pitch device being moved out of the side bore of the proximal part and into the side bore of the distal part and engaging with the catch device;

the pitch device having an interior bore that extends into the tip of the pitch device and openings in opposite sides of the pitch device adjacent the tip of the pitch device that intersect with the interior bore; and, the catch device having a proximal exterior surface portion that is dimensioned to be inserted into the interior bore of the pitch device and tabs on the proximal exterior surface portion of the catch device that extend into the openings in the opposite sides of the pitch device whereby the catch device catches and holds to the pitch device.

9. A surgical instrument comprising:

an instrument housing comprising a proximal part and a distal part;

the proximal part having a length between a proximal end surface of the proximal part and a distal end surface of the proximal part, the proximal part having a bridge bore extending through the length of the proximal part from the proximal end surface of the proximal part to the distal end surface of the proximal part, the proximal part having a side bore extending through the length of the proximal part from the proximal end surface of the proximal part to the distal end surface of the proximal part;

the distal part having a length between a proximal end surface of the distal part and a distal end surface of the distal part, the distal part having a side bore extending into the distal part from the proximal end surface of the distal part, the distal part having a slot extending into the distal part from the proximal end surface of the distal part, the slot being positioned adjacent the side bore and connecting to the side bore of the distal part;

a bridge adjustably connecting the proximal part and the distal part, the bridge having a length that extends from a proximal end surface of the bridge, through the bridge bore of the proximal part and to a distal end of the bridge that is secured to the distal part the bridge adjustably connecting the proximal part and the distal part with the side bore of the proximal part aligned with the side bore of the distal part, the bridge being adjustable to selectively move the proximal part and the distal part away from each other and the bridge being adjustable to selectively move the proximal part and the distal part toward each other;

a pitch device in the side bore of the proximal part, the pitch device having a length that extends from a handle of the pitch device, through the side bore of the proximal part to a tip of the pitch device positioned inside the side bore of the proximal part;

a catch device in the side bore of the distal part;

a suture in the slot of the distal part, the suture being connected to the catch device;

the catch device being operable to catch and hold to the tip of the pitch device in response to the handle of the pitch device being moved toward the proximal end surface of the proximal part and the tip of the pitch device being moved out of the side bore of the proximal part and into the side bore of the distal part and engaging with the catch device;

the side bore extending through the length of the proximal part being a first side bore extending through the length of the proximal part, the proximal part having a second side bore extending through the length of the proximal part from the proximal end surface of the proximal part to the distal end surface of the proximal part;

the side bore extending into the distal part being a first side bore extending into the distal part from the proximal end surface of the distal part, the distal part having a second side bore extending into the distal part from the proximal end surface of the distal part;

the pitch device in the side bore of the proximal part being a first pitch device in the first side bore of the proximal part;

a second pitch device in the second side bore of the proximal part, the second pitch device having a length that extends from a handle of the second pitch device, through the second side bore of the proximal part to a tip of the second pitch device positioned inside the second side bore of the proximal part;

the catch device in the side bore of the distal part being a first catch device in the first side bore of the distal part;

a second catch device in the second side bore of the distal part;

the suture in the slot of the distal part being connected to the first catch device and the second catch device;

the second catch device being operable to catch and hold to the tip of the second pitch device in response to the handle of the second pitch device being moved toward the proximal end surface of the proximal part and the tip of the second pitch device being moved out of the second side bore of the proximal part and into the second side bore of the distal part and engaging with the second catch device;

the first catch device having a resilient tube with a cylindrical interior surface that surrounds an interior bore of the first catch device and a pair of tabs that project inwardly toward each other from the cylindrical interior surface and into the interior bore;

the second catch device having a resilient tube with a cylindrical interior surface that surrounds an interior bore of the second catch device and a pair of tabs that project inwardly from the cylindrical interior surface and into the interior bore of the second catch device;

the first pitch device having a circumferential notch adjacent the tip of the first pitch device, the circumferential notch being dimensioned to receive the tabs of the first catch device in the circumferential notch when the tip of the first pitch device is inserted into the tube of the first catch device whereby the first catch device catches and holds to the first pitch device; and, the second pitch device having a circumferential notch adjacent the tip of the second pitch device, the circumferential notch being dimensioned to receive the tabs of the second catch device in the circumferential notch when the tip of the second pitch device is inserted into the tube of the second catch device whereby the second catch device catches and holds to the second pitch device.

10. A surgical instrument comprising:

an instrument housing comprising a proximal part and a distal part;

the proximal part having a length between a proximal end surface of the proximal part and a distal end surface of the proximal part, the proximal part having a bridge bore extending through the length of the proximal part from the proximal end surface of the proximal part to the distal end surface of the proximal part, the proximal part having a side bore extending through the length of the proximal part from the proximal end surface of the proximal part to the distal end surface of the proximal part;

the distal part having a length between a proximal end surface of the distal part and a distal end surface of the distal part, the distal part having a side bore extending into the distal part from the proximal end surface of the distal part, the distal part having a slot extending into the distal part from the proximal end surface of the distal part, the slot being positioned adjacent the side bore and connecting to the side bore of the distal part;

a bridge adjustably connecting the proximal part and the distal part, the bridge having a length that extends from a proximal end surface of the bridge, through the bridge bore of the proximal part and to a distal end of the bridge that is secured to the distal part, the bridge adjustably connecting the proximal part and the distal part with the side bore of the proximal part aligned with the side bore of the distal part, the bridge being adjustable to selectively move the proximal part and the distal part away from each other and the bridge being adjustable to selectively move the proximal part and the distal part toward each other;

a pitch device in the side bore of the proximal part, the pitch device having a length that extends from a handle of the pitch device, through the side bore of the proximal part to a tip of the pitch device positioned inside the side bore of the proximal part;

a catch device in the side bore of the distal part;

a suture in the slot of the distal part, the suture being connected to the catch device;

the catch device being operable to catch and hold to the tip of the pitch device in response to the handle of the pitch device being moved toward the proximal end surface of the proximal part and the tip of the pitch device being moved out of the side bore of the proximal part and into the side bore of the distal part and engaging with the catch device;

the side bore extending through the length of the proximal part being a first side bore extending through the length of the proximal part, the proximal part having a second side bore extending through the length of the proximal part from the proximal end surface of the proximal part to the distal end surface of the proximal part;

the side bore extending into the distal part being a first side bore extending into the distal part from the proximal end surface of the distal part, the distal part having a second side bore extending into the distal part from the proximal end surface of the distal part;

the pitch device in the side bore of the proximal part being a first pitch device in the first side bore of the proximal part;

a second pitch device in the second side bore of the proximal part, the second pitch device having a length that extends from a handle of the second pitch device, through the second side bore of the proximal part to a tip of the second pitch device positioned inside the second side bore of the proximal part;

the catch device in the side bore of the distal part being a first catch device in the first side bore of the distal part;

a second catch device in the second side bore of the distal part;

the suture in the slot of the distal part being connected to the first catch device and the second catch device;

the second catch device being operable to catch and hold to the tip of the second pitch device in response to the handle of the second pitch device being moved toward the proximal end surface of the proximal part and the tip of the second pitch device being moved out of the second side bore of the proximal part and into the second side bore of the distal part and engaging with the second catch device;

the first pitch device having an interior bore that extends into the tip of the first pitch device and openings in opposite sides of the first pitch device adjacent the tip of the first pitch device that intersect with the interior bore;

the second pitch device having an interior bore that extends into the tip of the second pitch device and openings in opposite sides of the second pitch device adjacent the tip of the second pitch device that intersect with the interior bore of the second pitch device;

the first catch device having a proximal exterior surface portion that is dimensioned to be inserted into the interior bore of the first pitch device and tabs on the proximal exterior surface portion of the first catch device that extend into the openings in the opposite sides of the first pitch device whereby the first catch device catches and holds to the first pitch device; and, the second catch device having a proximal exterior surface portion that is dimensioned to be inserted into the interior bore of the second pitch device and tabs on the proximal exterior surface portion of the second catch device that extend into the openings in the opposite sides of the second pitch device whereby the second catch device catches and holds to the second pitch device.

11. A surgical instrument comprising:

an instrument housing comprising a proximal part and a distal part;

the proximal part having a length between a proximal end surface of the proximal part and a distal end surface of the proximal part, the proximal part having a center bore extending through the length of the proximal part from the proximal end surface of the proximal part to the distal end surface of the proximal part, the proximal part having a first side bore extending through the length of the proximal part from the proximal end surface of the proximal part to the distal end surface of the proximal part, the proximal part having a second side bore extending through the length of the proximal part from the proximal end surface of the proximal part to the distal end surface of the proximal part, the first side bore of the proximal part and the second side bore of the proximal part being on opposite sides of the center bore of the proximal part;

the distal part having a length between a proximal end surface of the distal part and a distal end surface of the distal part, the distal part having a first side bore extending into the distal part from the proximal end surface of the distal part, the distal part having a second side bore extending into the distal part from the proximal end surface of the distal part, the distal part having a slot extending into the distal part from the proximal end surface of the distal part, the slot connecting the first side bore of the distal part and the second side bore of the distal part;

a bridge adjustably connecting the proximal part and the distal part, the bridge having a length that extends from a proximal end surface of the bridge positioned outside the proximal part, through the center bore of the proximal part and to a distal end of the bridge that is secured to the distal part between the first side bore of the distal part and the second side bore of the distal part, the bridge adjustably connecting the proximal part and the distal part with the first side bore of the proximal part aligned with the first side bore of the distal part and with the second side bore of the proximal part aligned with the second side bore of the distal part, the bridge being adjustable to selectively move the proximal part and the distal part away from each other in response to the proximal end surface of the bridge being moved toward the proximal end surface of the proximal part and the bridge being adjustable to selectively move the proximal part and the distal part toward each other in response to the proximal end surface of the bridge being moved away from the proximal end surface of the proximal part;

a first pitch device in the first side bore of the proximal part, the first pitch device having a length that extends from a handle of the first pitch device positioned outside the proximal part, through the first side bore of the proximal part to a needle tip of the first pitch device positioned inside the first side bore of the proximal part;

a second pitch device inside the second side bore of the proximal part, the second pitch device having a length that extends from a handle of the second pitch device positioned outside the proximal part, through the second side bore of the proximal part to a needle tip of the second pitch device positioned inside the second side bore of the proximal part;

a first catch device in the first side bore of the distal part;

a second catch device in the second side bore of the distal part;

a suture in the slot of the distal part, the suture being connected to the first catch device and the second catch device;

the first catch device being operable to catch and hold to the needle tip of the first pitch device in response to the handle of the first pitch device being moved toward the proximal end surface of the proximal part and the needle tip of the first pitch device being moved out of the first side bore of the proximal part and into the first side bore of the distal part and engaging with the first catch device;

the second catch device being operable to catch and hold to the needle tip of the second pitch device in response to the handle of the second pitch device being moved toward the proximal end surface of the proximal part and the needle tip of the second pitch device being moved out of the second side bore of the proximal part and into the second side bore of the distal part and engaging with the second catch device;

the first catch device having a resilient tube with a cylindrical interior surface that surrounds an interior bore of the first catch device and a pair of tabs that project inwardly toward each other from the cylindrical interior surface and into the interior bore;

the second catch device having a resilient tube with a cylindrical interior surface that surrounds an interior bore of the second catch device and a pair of tabs that project inwardly from the cylindrical interior surface and into the interior bore of the second catch device;

the first pitch device having a circumferential notch adjacent the needle tip of the first pitch device, the circumferential notch being dimensioned to receive the tabs of the first catch device in the circumferential notch when the needle tip of the first pitch device is inserted into the tube of the first catch device whereby the first catch device catches and holds to the first pitch device; and, the second pitch device having a circumferential notch adjacent the needle tip of the second pitch device, the circumferential notch being dimensioned to receive the tabs of the second catch device in the circumferential notch when the needle tip of the second pitch device is inserted into the tube of the second catch device whereby the second catch device catches and holds to the second pitch device.

12. A surgical instrument comprising:

an instrument housing comprising a proximal part and a distal part;

the proximal part having a length between a proximal end surface of the proximal part and a distal end surface of the proximal part, the proximal part having a center bore extending through the length of the proximal part from the proximal end surface of the proximal part to the distal end surface of the proximal part, the proximal part having a first side bore extending through the length of the proximal part from the proximal end surface of the proximal part to the distal end surface of the proximal part, the proximal part having a second side bore extending through the length of the proximal part from the proximal end surface of the proximal part to the distal end surface of the proximal part, the first side bore of the proximal part and the second side bore of the proximal part being on opposite sides of the center bore of the proximal part;

the distal part having a length between a proximal end surface of the distal part and a distal end surface of the distal part, the distal part having a first side bore extending into the distal part from the proximal end surface of the distal part, the distal part having a second side bore extending into the distal part from the proximal end surface of the distal part, the distal part having a slot extending into the distal part from the proximal end surface of the distal part, the slot connecting the first side bore of the distal part and the second side bore of the distal part;

a bridge adjustably connecting the proximal part and the distal part, the bridge having a length that extends from a proximal end surface of the bridge positioned outside the proximal part, through the center bore of the proximal part and to a distal end of the bridge that is secured to the distal part between the first side bore of the distal part and the second side bore of the distal part, the bridge adjustably connecting the proximal part and the distal part with the first side bore of the proximal part aligned with the first side bore of the distal part end with the second side bore of the proximal part aligned with the second side bore of the distal part, the bridge being adjustable to selectively move the proximal part and the distal part away from each other in response to the proximal end surface of the bridge being moved toward the proximal end surface of the proximal part and the bridge being adjustable to selectively move the proximal part and the distal part toward each other in response to the proximal end surface of the bridge being moved away from the proximal end surface of the proximal part;

a first pitch device in the first side bore of the proximal part, the first pitch device having a length that extends from a handle of the first pitch device positioned outside the proximal part, through the first side bore of the proximal part to a needle tip of the first pitch device positioned inside the first side bore of the proximal part;

a second pitch device inside the second side bore of the proximal part, the second pitch device having a length that extends from a handle of the second pitch device positioned outside the proximal part, through the second side bore of the proximal part to a needle tip of the second pitch device positioned inside the second side bore of the proximal part;

a first catch device in the first side bore of the distal part;

a second catch device in the second side bore of the distal part;

a suture in the slot of the distal part, the suture being connected to the first catch device and the second catch device;

the first catch device being operable to catch and hold to the needle tip of the first pitch device in response to the handle of the first pitch device being moved toward the proximal end surface of the proximal part and the needle tip of the first pitch device being moved out of the first side bore of the proximal part and into the first side bore of the distal part and engaging with the first catch device;

the second catch device being operable to catch and hold to the needle tip of the second pitch device in response to the handle of the second pitch device being moved toward the proximal end surface of the proximal part and the needle tip of the second pitch device being moved out of the second side bore of the proximal part and into the second side bore of the distal part and engaging with the second catch device;

the first pitch device having an interior bore that extends into the needle tip of the first pitch device and openings in opposite sides of the first pitch device adjacent the needle tip of the first pitch device that intersect with the interior bore;

the second pitch device having an interior bore that extends into the needle tip of the second pitch device and openings in opposite sides of the second pitch device adjacent the needle tip of the second pitch device that intersect with the interior bore of the second pitch device;

the first catch device having a proximal exterior surface portion that is dimensioned to be inserted into the interior bore of the first pitch device and tabs on the proximal exterior surface portion of the first catch device that extend into the openings in the opposite sides of the first pitch device whereby the first catch device catches and holds to the first pitch device; and, the second catch device having a proximal exterior surface portion that is dimensioned to be inserted into the interior bore of the second pitch device and tabs on the proximal exterior surface portion of the second catch device that extend into the openings in the opposite sides of the second pitch device whereby the second catch device catches and holds to the second pitch device.

13. A method of closing a trocar puncture wound in an abdominal wall, the method comprising:

inserting a surgical instrument having a proximal part and a distal part through the trocar puncture wound in the abdominal wall until the distal part of the instrument and a portion of the proximal part of the instrument are positioned in an abdominal cavity;

manually manipulating a bridge of the surgical instrument causing the distal part of the instrument to move away from the proximal part of the instrument and exposing a portion of the bridge that extends between the distal part of the instrument and the proximal part of the instrument;

pulling the proximal part of the instrument away from the trocar puncture wound in the abdominal wall until the portion of the bridge between the distal part of the surgical instrument and the proximal part of the surgical instrument is moved into the trocar puncture wound, causing a portion of the abdominal wall surrounding the trocar puncture wound to contract around the portion of the bridge;

moving the distal part of the surgical instrument toward the proximal part of the surgical instrument until the portion of the abdominal wall surrounding the trocar puncture wound and surrounding the portion of the bridge is engaged and secured between the distal part of the surgical instrument and the proximal part of the surgical instrument;

moving a first pitch device through the proximal part of the surgical instrument toward the distal part of the surgical instrument causing a tip of the first pitch device to penetrate through the portion of the abdominal wall surrounding the trocar puncture wound and secured between the distal part of the surgical instrument and the proximal part of the surgical instrument and causing the tip of the first pitch device to move into a first catch device in the distal part of the surgical instrument whereby the first catch device catches the first pitch device;

moving a second pitch device through the proximal part of the surgical instrument toward the distal part of the surgical instrument causing a tip of the second pitch device to penetrate through the portion of the abdominal wall surrounding the trocar puncture wound and secured between the distal part of the surgical instrument and the proximal part of the surgical instrument and causing the tip of the second pitch device to move into a second catch device in the distal part of the surgical instrument whereby the second catch device catches the second pitch device; and, moving the first pitch device and the second pitch device through the proximal part of the surgical instrument away from the distal part of the surgical instrument causing the first catch device and the second catch device to be withdrawn from the distal part of the surgical instrument and through the portion of the abdominal wall surrounding the trocar puncture wound and secured between the distal part of the surgical instrument and the proximal part of the surgical instrument and pulling a length of suture connected between the first catch device and the second catch device through the portion of the abdominal wall surrounding the trocar puncture wound and secured between the distal part of the surgical instrument and the proximal part of the surgical instrument on opposite sides of the trocar puncture wound in the abdominal wall.

14. The method of claim 13, further comprising:

pulling a first end of the suture connected to the first catch device and a second end of the suture connected to the second catch device from outside the abdominal wall and causing a portion of the suture extending across the trocar puncture wound in the abdominal wall inside the abdominal cavity to close the trocar puncture wound in the abdominal wall.

15. The method of claim 14, further comprising:

tying off the first end of the suture and the second end of the suture outside the abdominal wall and completing stitching closed the trocar puncture wound in the abdominal wall.

\* \* \* \* \*